United States Patent [19]

Effland et al.

[11] Patent Number: 4,806,554
[45] Date of Patent: Feb. 21, 1989

[54] PYRAZOL AND INDAZOLPYRIDINAMINES

[75] Inventors: Richard C. Effland; Joseph T. Klein, both of Bridgewater, N.J.

[73] Assignee: Hoechst-Roussel Pharmaceuticals, Inc., Somerville, N.J.

[21] Appl. No.: 141,852

[22] Filed: Jan. 11, 1988

[51] Int. Cl.[4] .................. C07D 401/04; A61K 31/415
[52] U.S. Cl. .................... 514/338; 514/341; 514/318; 514/253; 514/252; 514/236.5; 514/234.5; 546/279; 546/271; 546/193; 544/124; 544/360
[58] Field of Search ...................... 546/279, 271, 193; 544/124, 360; 514/338, 341, 318, 237, 253, 252

[56] References Cited

FOREIGN PATENT DOCUMENTS 0226099 6/1987 European Pat. Off. .

OTHER PUBLICATIONS

Petrow, J. Chem. Soc., 1945, 927–928.
Wesseling, New England Journal of Medicine, 310(15), 988–989, '84.
Delange et al., Cur. J. Med. Chem–Chin. Ther., 15(4), 299–304, 1980.
Miller et al., J. Med. Chem., 13(5), 1022–1023, 1970.
Adger et al., J. Chem. Soc., Perkin Trans. I, 31–40 (1975).
Arya et al., Indian J. Chem., 15B, 625–628, 1977.
Khan et al., J. Chem. Soc. (C), 85–91, 1970.
Boulton et al., J. Chem. Soc., Perkin Trans. I, 1249–1253, 1986.
Neunhoeffer et al., Ann Chem., 1732–1751 (1985).
Ohsawa et al., J. Org. Chem., 50: 5520–5523 (1985).
Biuix et al., Tetrahedron Lett., 5485–5487 (1985).
Koga et al., Tetrahedron Lett., 1291 (1978).
Clemo et al., J. Chem. Soc., 1739 (1934).
Nakajima et al., J. Org. Chem., vol. 43, No. 13, 2683–2696, 1978.

Primary Examiner—Jane T. Fan
Attorney, Agent, or Firm—Tatsuya Ikeda

[57] ABSTRACT

There are described compounds of the formula

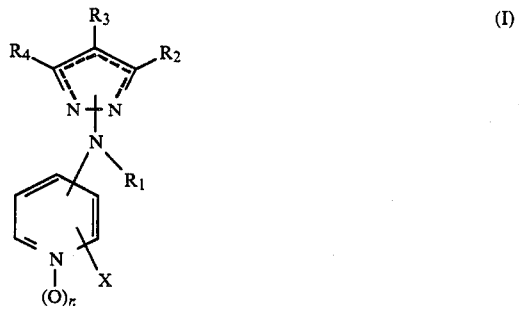

(I)

where $n$ is 0 or 1;
$R_1$ is independently hydrogen, loweralkyl, loweralkenyl, loweralkynyl, loweralkoxycarbonylloweralkyl, loweralkylaminocarbonylloweralkyl, aminocarbonylloweralkyl, arylloweralkyl, phenyl, nitrophenyl, cyanophenyl, trifluoromethylphenyl, aminophenyl, loweralkanoylaminophenyl, loweralkoxycarbonyl, arylloweralkoxycarbonyl, aryloxycarbonyl, loweralkylaminocarbonyl, arylloweralkylaminocarbonyl, arylaminocarbonyl, alkanoyl, arylloweralkanoyl, aroyl, alkenoyl, alkynoyl or —$R_5$—NR'R" where $R_5$ is loweralkylene, loweralkenylene or loweralkynylene and R' and R" are each independently loweralkyl or alternatively the group —NR'R" as a whole is 1-pyrrolidinyl, 1-piperidinyl, 4-morpholinyl, 4-loweralkyl-1-piperazinyl or 4-aryl-1-piperazinyl;
$R_2$ is hydrogen or loweralkyl;
$R_3$ and $R_4$ are each independently hydrogen or loweralkyl, or alternatively $R_3$ and $R_4$ taken together form —CH=CH—CH=CH— so that the moiety

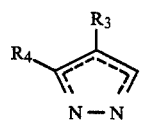

becomes an indazole ring; and
X is hydrogen, nitro, amino, halogen, loweralkanoylamino, arylloweralkanoylamino, aroylamino, alkylamino, arylloweralkylamino, loweralkyl, and cyano; which compounds are useful as analgesic and antidepressant agents.

25 Claims, No Drawings

PYRAZOL AND INDAZOLPYRIDINAMINES

The present invention relates to novel compounds of the formula

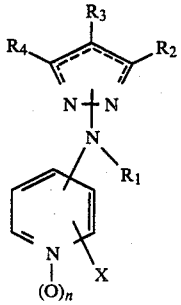
(I)

n is 0 or 1;

$R_1$ is independently hydrogen, loweralkyl, loweralkenyl, loweralkynyl, loweralkoxycarbonylloweralkyl, loweralkylaminocarbonylloweralkyl, aminocarbonylloweralkyl, arylloweralkyl, phenyl, nitrophenyl, cyanophenyl, trifluoromethylphenyl, aminophenyl, loweralkanoylaminophenyl, loweralkoxycarbonyl, arylloweralkoxycarbonyl, aryloxycarbonyl, loweralkylaminocarbonyl, arylloweralkylaminocarbonyl, arylaminocarbonyl, alkanoyl, arylloweralkanoyl, aroyl, alkenoyl, alkynoyl or —$R_5$—NR'R" where $R_5$ is loweralkylene, loweralkenylene or loweralkynylene and R' and R" are each independently loweralkyl or alternatively the group —NR'R" as a whole is 1-pyrrolidinyl, 1-piperidinyl, 4-morpholinyl, 4-loweralkyl-1-piperazinyl or 4-aryl-1-piperazinyl;

$R_2$ is hydrogen or loweralkyl;

$R_3$ and $R_4$ are each independently hydrogen or loweralkyl, or alternatively $R_3$ and $R_4$ taken together form —CH=CH—CH=CH— so that the moiety

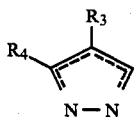

becomes an indazole ring; and

X is hydrogen, nitro, amino, halogen, loweralkanoylamino, arylloweralkanoylamino, aroylamino, alkylamino, arylloweralkylamino, loweralkyl, and cyano; which compounds are useful as analgesic and antidepressant agents.

Compounds of formula I subsumes two types of compounds depicted below:

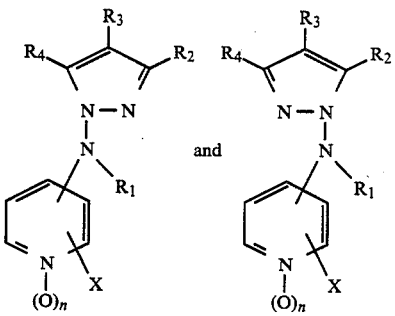

Throughout the specification and the appended claims, a given chemical formula or name shall encompass all stereo, optical, and geometrical isomers thereof where such isomers exist, as well as pharmaceutically acceptable acid addition salts thereof and solvates thereof such as for instance hydrates.

The following general rules of terminology shall apply throughout the specification and appended claims.

Unless otherwise stated or indicated, the term loweralkyl denotes a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

Unless otherwise stated or indicated, the term aryl shall mean a phenyl group having 0, 1, 2 or 3 substituents each of which being independently loweralkyl, loweralkoxy, halogen, $CF_3$, $NO_2$ or CN.

Unless otherwise stated or indicated, the term alkyl shall mean a saturated hydrocarbon group of 1 to 20 carbon atoms, the term alkenyl shall mean a hydrocarbon group of 1–20 carbon atoms having one or more carbon-carbon double bonds, and the term alkynyl shall mean a hydrocarbon group of 1–20 carbon atoms having one or more carbon-carbon triple bonds.

The term loweralkanoic acid shall mean a carboxylic acid in which the carboxyl group is attached to hydrogen or an alkyl group of from 1 to 5 carbon atoms.

The term loweralkanoyl shall mean a group obtained by removing a hydroxy group from the carboxyl group of a loweralkanoic acid, and thus it includes for instance formyl, acetyl and the like.

The term arylloweralkanoyl shall mean a loweralkanoyl group having an aryl substituent thereon, the term loweralkanoyl and aryl having the respective meanings defined above.

The term aroyl shall mean arylcarbonyl, an example being benzoyl.

The term arylloweralkyl shall mean a loweralkyl group having an aryl substituted thereon, the terms loweralkyl and aryl having the respective meanings defined above.

The terms alkanoyl, alkenoyl and alkynoyl shall mean groups obtained by removing a hydroxy group from the carboxyl group of alkanoic acid, alkenoic acid and alkynoic acid, respectively. Thus, for instance, linoleyl group derived from linoleic acid is an example of the term alkenoyl as defined above.

The term acyl shall mean loweralkanoyl or arylloweralkanoyl as defined above.

The compounds of formula (I) of this invention can be synthesized by following or combining one or more of the steps described below, not necessarily in the order presented. Throughout the description of the synthetic steps, the definitions of $R_1$ through $R_5$, R', R'', X and n are as given above unless otherwise stated or indicated, and other nomenclatures appearing below shall have the same meanings defined in their respective first appearances unless otherwise stated or indicated.

STEP A

A compound of formula (II) where $R_6$ is H or loweralkyl is reacted with a compound of formula (III) where Hal is chlorine or fluorine and $R_7$ is H, $NO_2$, halogen or loweralkyl to afford a compound of formula (IV).

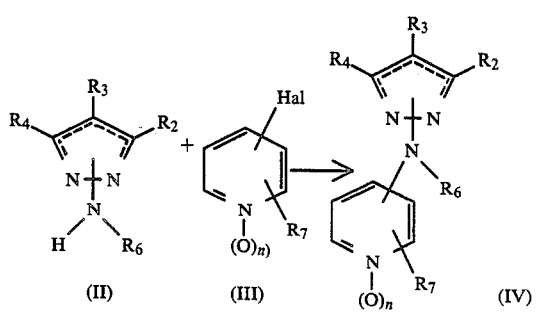

Said reaction is typically conducted in an ethereal solvent such as bis(2-methoxyethyl)ether, diethyl ether, dimethoxy ether, dioxane or tetrahydrofuran or polar aprotic solvent such as dimethylformamide, dimethylacetamide, hexamethylphosphoramide or dimethylsulfoxide or protic solvent such as ethanol or isopropanol at a temperature of between about 20° C. and 150° C.

STEP B

A compound of formula IVa obtained from STEP A is treated with a strong base such as sodium hydride or potassium hydride in a suitable solvent such as polar aprotic solvent including dimethylformamide, dimethylsulfoxide and ethereal solvents or aromatic hydrocarbon at a temperature of between about −10° and 50°, preferably 0°–25° to form the anion of IVa, which is reacted with a chloride compound of the formula $R_8$—Cl, where $R_8$ is loweralkyl, loweralkoxycarbonylloweralkyl, loweralkenyl, loweralkynyl, arylloweralkyl, loweralkoxycarbonyl, arylloweralkoxycarbonyl or aryloxycarbonyl at a temperature of between about −10° and 80°, preferably between 0° and 25° to obtain a compound of formula V.

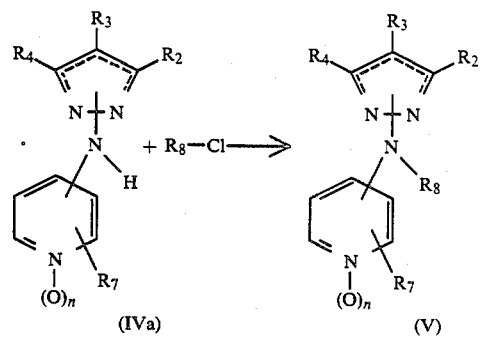

STEP C

The anion of compound IVa prepared as in STEP B is reacted with fluoro-nitrobenzene, cyano-fluorobenzene or fluoro-trifluoromethylbenzene of the formula

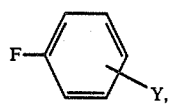

where Y is nitro, cyano or trifluoromethyl to afford a compound of formula VI below. Said reaction is conducted in substantially the same manner as in STEP B.

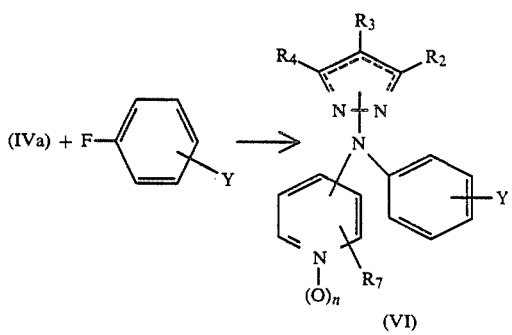

STEP D

Compound IVa is reacted with a loweralkyl isocyanate, arylloweralkyl isocyanate or aryl isocyanate of the formula $R_9NCO$ where $R_9$ is loweralkyl, arylloweralkyl or aryl to afford a compound of formula VII.

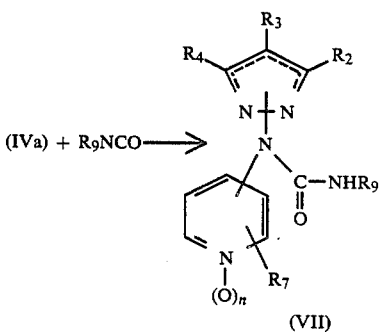

Said reaction is typically conducted in a suitable solvent such as aromatic hydrocarbon including benzene, toluene and the like, halogenated hydrocarbon or ethereal solvent at a temperature of about 0°–80°, preferably 30°–60° C.

STEP E

Compund IVa is reacted with an alkanoyl chloride, arylloweralkanoyl chloride, aroyl chloride, alkenoyl chloride or alkynoyl chloride of formula (VIII) where $R_{10}$ is alkyl, arylloweralkyl, aryl, alkenyl or alkynyl to afford a compound of formula (IX). Said reaction is typically conducted in substantially the same manner as in STEP D.

(IVa) + $R_{10}$COCl ⟶ (IX)
(VIII)

Where the compound $R_{10}$COCl is not commercially available, it is prepared from the corresponding carboxylic acid $R_{10}$COOH and thionyl chloride in a suitable solvent, for instance, in benzene at the reflux temperature.

STEP F

As an alternative to STEP A or B, a compound of formula (IVb) where $R_{11}$ is loweralkyl can be prepared by reacting compound IVa with a strong base such as sodium hydride or potassium hydride and then reacting the product with a diloweralkyl sulfate of the formula $(R_{11})_2SO_4$. Said two steps are conducted under substantially the same conditions as those used in STEP B.

(IVA) + NaH $\xrightarrow{(R_{11})_2SO_4}$ (IVb)

STEP G

A compound of formula Va where —R— is an alkylene group of one to three carbons obtained in STEP B is subjected to Mannich reaction with formaldehyde and a secondary amine of the formula HNR'R", where R' and R" are independently loweralkyl or alternatively —NR'R" taken together is 1-pyrrolidinyl, 1-piperidinyl, 4-morphlinyl, 4-loweralkyl-1-piperazinyl or 4-aryl-1-piperazinyl to afford a compound of formula X.

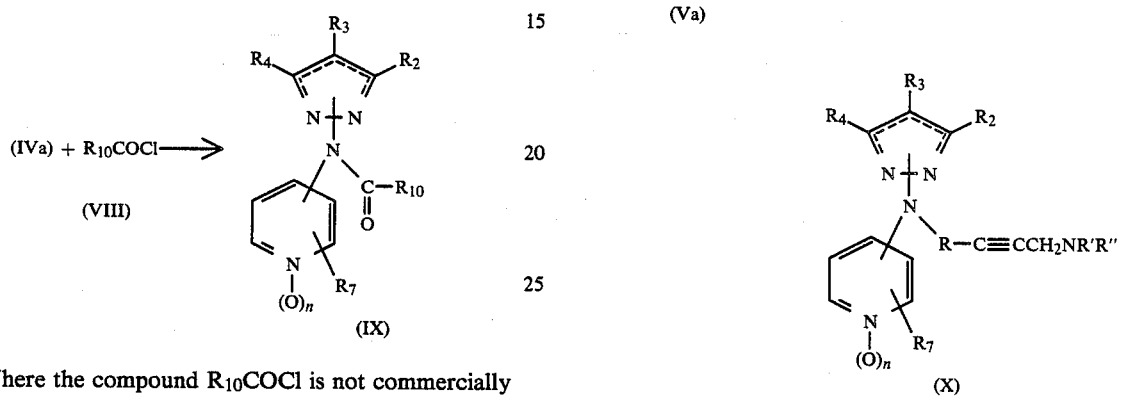
(Va)

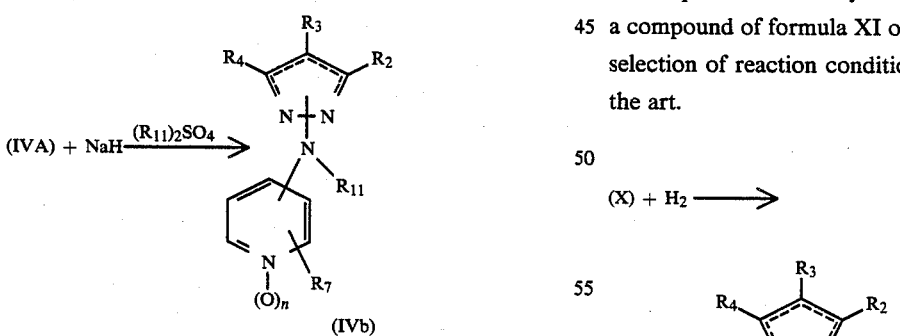
(X)

The above reaction can be conducted under conditions usually used in the art for carrying out Mannich reactions. Typically, it is conducted by preparing a mixture of compound Va, paraformaldehyde, HNR'R", cuprous chloride (used as a catalyst) and a suitable medium including ethereal solvents such as dioxane, and heating the mixture at 25°–100°.

STEP H

Compound X is catalytically hydrogenated to afford a compound of formula XI or XII by making a suitable selection of reaction conditions in a manner known to the art.

(X) + $H_2$ ⟶

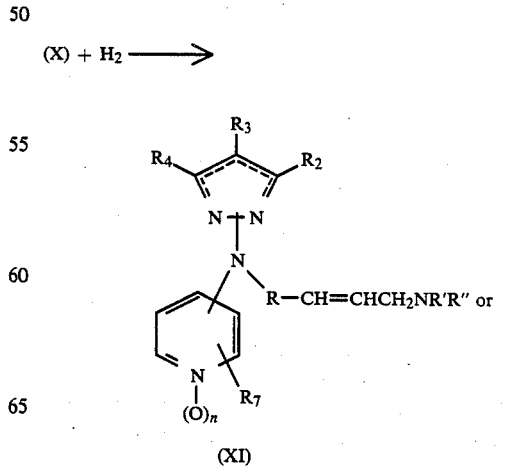
(XI)

-continued

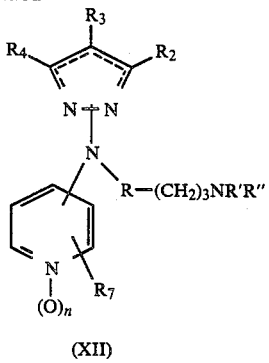

(XII)

STEP I

A compound of formula XIII which is prepared by use of one or more of the reaction steps described in this specification is catalytically hydrogenated with hydrogen gas and a suitable catalyst such as palladium on carbon to afford a compound for formula XIV.

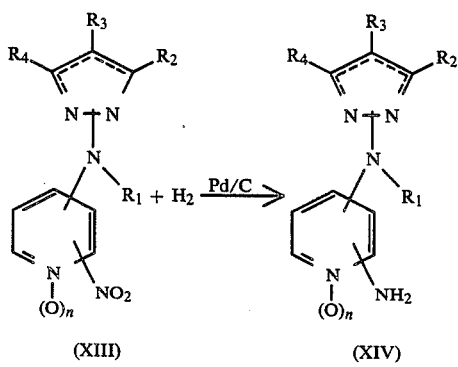

(XIII)    (XIV)

Said catalytic hydrogenation is typically conducted in a suitable solvent such as loweralkanol or loweralkyl ester of loweralkanoic acid at a temperature of 20°–50° C.

STEP J

Compound XIV is reacted with phenyl formate to afford a compound of formula XV.

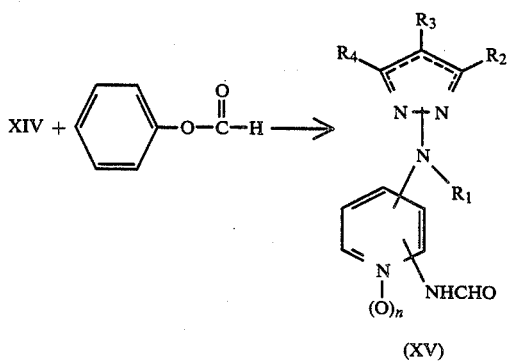

(XV)

Typically said reaction is conducted by stirring a solution of compound XIV in excess phenyl formate at a temperature of about 20°–50° C. The same reaction can also be conducted with loweralkyl formate under substantially the same conditions.

STEP K

Compound XIV is reacted with an acyl chloride of the formula $R_{12}COCl$ or acid anhydride of the formula $R_{12}CO$—O—$COR_{12}$ where $R_{12}$ is loweralkyl, arylloweralkyl or aryl to afford a compound of formula XVI.

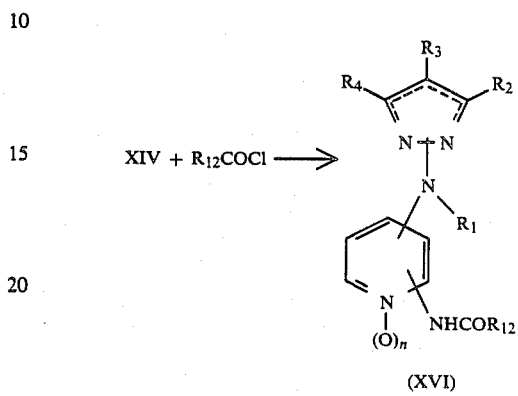

(XVI)

Said reaction is conducted under substantially the same conditions as used in STEP E.

STEP L

As an alternative to the foregoing steps, a compound of formula XVII where $R_{13}$ is loweralkyl and $R_1$ is loweralkyl, arylloweralkyl, phenyl, nitrophenyl or trifluoromethylphenyl can be prepared by reacting a compound of formula IVc with a loweralkyl lithium of the formula $R_{13}Li$.

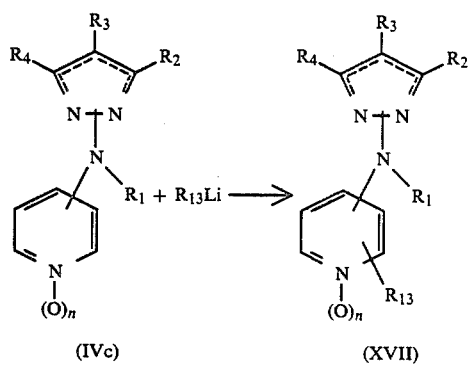

(IVc)    (XVII)

Said reaction is usually conducted in a suitable solvent such as ethereal solvent, preferably tetrahydrofuran at a temperature of between about −10° and 50° C.

STEP M

Substantially the same hydrogenation technique as described in STEP J can be used to hydrogenate a compound of formula XVIII below which is obtained from one of the foregoing steps to afford a compound of formula XIX below.

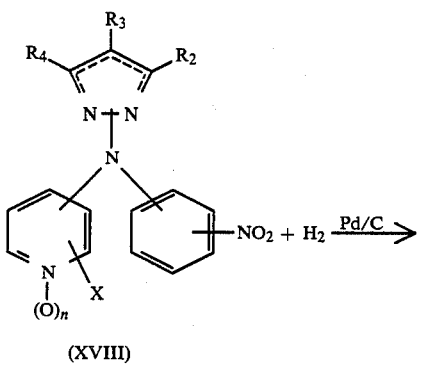

(XVIII)

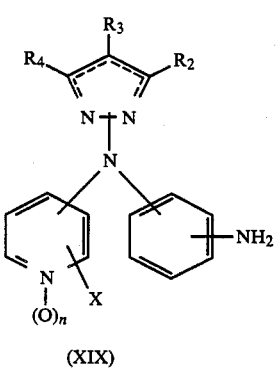

(XIX)

STEP N

Substantially the same reaction technique as described in STEP K can be used to convert compound XIX to a compound of formula XX below.

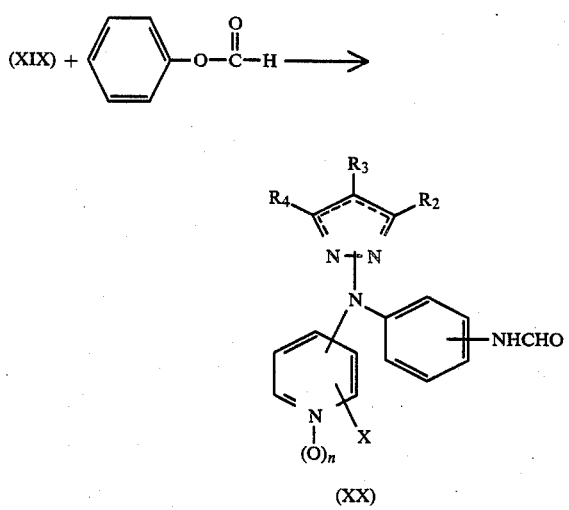

(XX)

STEP O

Substantially the same reaction technique as described in STEP L can be used to convert compound XIX to a compound of formula XXI below.

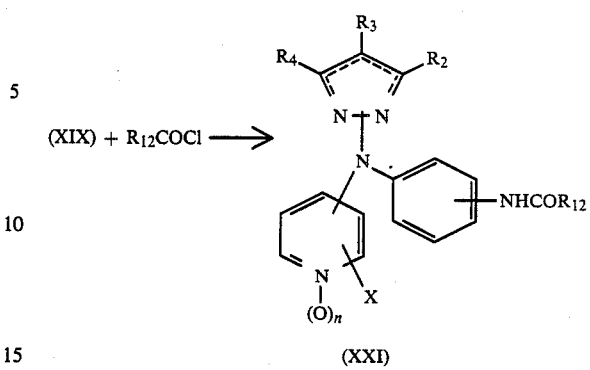

(XXI)

STEP P

For the purpose of preparing a compound of formula I where $R_1$ is aminocarbonylloweralkyl, a compound of formula I where $R_1$ is loweralkoxycarbonylloweralkyl (preferably ethoxycarbonylloweralkyl) is reacted with ammonia in a manner known to the art.

The compounds of formula I of this invention exhibit antidepressant activities. The antidepressant activities have been evaluated in this invention on the basis of prevention of tetrabenazine-induced ptosis in mice. The test method and results are described below.

PREVENTION OF TETRABENAZINE-INDUCED PTOSIS IN MICE

Tetrabenazine (TBZ) induces behavioral depression with concomitant ptosis in mice similar to reserpine. Antidepressant compounds, both monoamineoxidase inhibitors and tricyclics, are known to prevent or antagonize these effects and the degree of antagonism correlates with clinical efficacy. The prevention of TBZ-induced ptosis in mice is used as a preliminary screen for possible antidepressant activity. The method used in this invention is as follows:

Male mice weighing 20 to 30 grams are used in test groups of five subjects. All compounds are dissolved or suspended with a suitable surfactant in distilled water and administered in volumes of 10 ml/kg of body weight. TBZ solution is made from the methanesulfonate salt and the concentration is adjusted to enable administration of 60 mg/kg of base by intraperitoneal (i.p.) injection.

The pretreatment time is measured from the time of dosing to observation. Therefore, when a 30-minute pretreat is utilized, drug and TBZ are given simultaneously. A control group received solvent and TBZ at intervals identical to drug group. For a primary screen, the drug is administered i.p. and a group size of five is utilized. Eight animals/group are used for a dose range.

Thirty minutes after TBZ, the subjects are placed in individual plastic containers (10.5×8×6 inches) in the presence of white noise and one minute after the transfer, they are scored for ptosis on the following scale: Eyes closed=4, eyes ¾ closed=3, eyes ½ closed=2, eyes ¼ closed=1, eyes open=0. The total score for each group of five in a primary screen will, therefore, be from 0 to 20 and these scores are used as indications of drug activity.

The vehicle control group score is used as a determinant of the validity of each test. If the control score is less than 17, the results are discarded and the test repeated. The calculation of percent inhibition of ptosis is:

$$\frac{(\text{Control Score} - \text{Drug Score}) \times 100\%}{\text{Control Score}}$$

For $ED_{50}$ estimation, four or five doses are administered in order to bracket the estimated value and only vehicle control scores of 27 to 32 are accepted to assure the accuracy of the $ED_{50}$ estimation.

Linear regression analysis is used to estimate $ED_{50}$ values and 95% confidence intervals.

The results of some of the compounds of this invention are shown in Table 1 along with a result for desipramine (prior art compound).

TABLE 1

| ANTIDEPRESSANT ACTIVITY | |
|---|---|
| Compound | $ED_{50}$ (mg/kg, p.o.) |
| N—(4-pyridinyl)-1H—indazol-1-amine maleate | 2.7 |
| N—(propyl)-N—(4-pyridinyl)-1H—indazol 1-amine maleate | 8.5 |
| (Reference Compound) Desipramine | 2.3 |

Compounds I of the present invention are also useful as analgesic agents due to their ability to alleviate pain in mammals. The activity of the compounds is demonstrated in the 2-phenyl-1,4-benzoquinone-induced writhing (PQW) test in mice, a standard assay for analgesia [Proc. Soc. Exptl. Biol. Med., 95, 729(1957)] and in modified Haffner's analgesia.

The latter assay is used to evaluate analgesic activity by measuring drug-induced changes in the sensitivity of mice to pressure stress by placing an artery clip (2½ inches long) on their tail. The procedure used is a modification of the test developed by Haffner, Dtsch. Med. Wschr. 55, 731 (1929), and it is described below:

METHOD

Male mice (Charles River, CD-1) from 18-30 grams are used for the test. An artery clip is applied to the root of the tail of a mouse (approximately ½ inch from the body) to induce pain. The animals quickly responds to this noxious stimuli by biting the clip or the location of the clip. This reaction time, the interval between stimulus onset and response, is recorded on 1/10 second increments by a stop watch.

For a time response, the screening dose (25 mg/kg) is administered subcutaneously (10 ml/kg) to the animal receiving food and water ad libitum before testing. Animals receiving the compound orally are fasted 18-24 hours before drug administration. Drug to be tested is prepared with distilled water and if insoluble, one drop of a surfactant is added.

Twenty-eight animals (seven/group) are administered the drug 15, 30, 45 and 60 minutes prior to testing.

The cut-off time (CO) is determined by taking the ($\bar{x}$) average +3 standard (SD) deviation of the combined response latencies of the control mice in all time periods.

$$CO = x + 3SD(seconds)$$

Any reaction time, in subsequent drug tests, which is greater than the CO (for the same time period) therefore exceeds 99% of normal Gaussian distribution and is called "positive response" indicative of analgesic activity. A time response indicates the period of greatest analgesic effect after dosing. The $ED_{50}$ is determined at the peak time of drug activity. A minimum of three dose groups are used. $ED_{50}$'s are calculated using computer analysis.

The results of some of the compounds of this invention are shown in Table 2 along with those of a prior art compound.

TABLE 2

| Compound | PQW (% Inhibition of writhing) | Modified Haffner's Analgesia ($ED_{50}$, mg/kg, s.c.) |
|---|---|---|
| N—(4-pyridinyl)-1H—indazol-1-amine maleate | 50% at 0.7 mg/kg, s.c. | 10.4 |
| N—(propyl)-N—(4-pyridinyl)-1H—indazol-1-amine maleate | 62% at 20 mg/kg, s.c. | |
| (Reference Compound) Pentazocin | 50% at 1.3 mg/kg, s.c. | 3.9 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0-300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parental therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, antibacterial agents such as benzyl alcohol or methyl parabens; antioxidants such as ascorbc acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in disposable syringes or multiple dose vials made of glass or plastic.

Examples of the compounds of this invention include:
N-(1H-Pyrazol-1-yl)-4-pyridinamine;
N-(Propyl)-N-(1H-pyrazol-1-yl)-4-pyridinamine;
N-(4-Pyridinyl)-1H-indazol-1-amine;
N-(4-Pyridinyl)-2H-indazol-2-amine;
N-(Propyl)-N-(4-pyridinyl)-1H-indazol-1-amine; and
N-(Propyl)-N-(4-pyridinyl)-2H-indazol-2-amine.

The following examples are presented in order to illustrate this invention.

EXAMPLE 1

N-(1H-Pyrazol-1-yl)-4-pyridinamine maleate

A solution of 1H-pyrazol-1-amine (14 g), 4-chloropyridine hydrochloride (26 g) and pyridine (13 g) in 125 ml of isopropanol was stirred at reflux for thirty minutes. An additional equivalent of pyridine and 4-chloropyridine hydrochloride was added and reflux was continued until all of the starting material was consumed. After one hour the reaction mixture was cooled, stirred with ice-water, basified with sodium carbonate and extracted with dichloromethane. The organic extract was washed with water and saturated sodium chloride solution, dried over anhydrous magnesium sulfate, filtered and concentrated to 20 g of oil. This was purified by flash chromatography (silica, ethyl acetate) to give 8.3 g of waxy residue. This was converted to the maleate salt in ethanol-ether to give 11 g of solid, mp 145° C. A 3 g sample was recrystallized from methanol-ether to give 2.9 g of white crystals, mp 147°–148°.

ANALYSIS: Calculated for $C_8H_8N_4.C_4H_4O_4$: 52.17%C, 4.38%H, 20.29%N. Found: 51.95%C, 4.28%H, 20.15%N.

EXAMPLE 2

N-(Propyl)-N-(1H-pyrazol-1-yl)-4-pyridinamine maleate

A solution of N-(1H-pyrazol-1-yl)-4-pyridinamine (4.6 g) in 25 ml of dimethylformamide was slowly added to an ice-cooled suspension of sodium hydride prepared by washing 1.4 g of 60% NaH dispersion in oil with hexane and suspending the residue in 5 ml of dimethylformamide. After the anion formation a solution of 1-bromopropane (4.2 g) in 5 ml of dimethylformamide was added. After one hour the reaction mixture was stirred with ice-water and extracted with dichloromethane. The organic extract was washed with water and saturated sodium chloride solution, dried over anhydrous magnesium sulfate, filtered and concentrated to 5.4 g of oil. This oil was purified by flash chromatography (silica, ethyl acetate) to give 4.8 g of yellow oil. This oil was converted to the maleate salt in ethanol-ether and recrystallized from methanol-ether to give 5.9 g of white crystals, mp 145°–146°.

ANALYSIS: Calculated for $C_{11}H_{14}N_4.C_4H_4O_4$: 56.59%C, 5.70%H, 17.60%N. Found: 56.45%C, 5.85%H, 17.57%N.

EXAMPLE 3

N-(4-Pyridinyl)-1H-indazol-1-amine maleate

A solution of 1H-indazol-1-amine (10.5 g), 4-chloropyridine hydrochloride (23.6 g) and pyridine (12.6 g) in 110 ml of isopropanol was stirred at reflux for one hour and thereafter cooled, stirred with ice-water, basified with sodium carbonate and extracted with dichloromethane. The organic extract was washed with water and saturated sodium chloride solution, dried over anhydrous magnesium sulfate, filtered and concentrated to 19 g of dark oil. This oil was purified by flash chromatography (silica, ethyl acetate) to give 3.8 g of red oil. This oil was converted to the maleate in ethanol-ether and recrystallized from methanol-ether to give 3.3 g of crystals, d 148°–150°.

ANALYSIS: Calculated for $C_{12}H_{10}N_4.C_4H_4O_4$: 58.89%C, 4.32%H, 17.17%N. Found: 58.71%C, 4.45%H, 16.98%N.

EXAMPLE 4

N-(4-Pyridinyl)-2H-indazol-2-amine maleate

A solution of 2H-indazol-2-amine (16 g), 4-chloropyridine hydrochloride (36 g) and pyridine (19 g) in 200 ml of isopropanol was stirred at reflux for 1.5 hours and thereafter cooled, stirred with ice-water, basified with sodium carbonate and extracted with dichloromethane. The organic extract was washed with water and saturated sodium chloride solution, dried over anhydrous magnesium sulfate, filtered and concentrated to 30 g of dark oil. This oil was purified by flash chromatography (silica, ethyl acetate) to give 9 g of orange oil. This oil was converted to the maleate salt in ethanol-ether to give 11 g of solid, d 174°–175°. A 3 g sample was recrystallized from methanol-ether to give 2.5 g of pale yellow solid.

ANALYSIS: Calculated for $C_{12}H_{10}N_4.C_4H_4O_4$: 58.89%C, 4.32%H, 17.17%N. Found: 58.78%C, 4.27%H, 17.06%N.

EXAMPLE 5

N-(Propyl)-N-(4-pyridinyl)-1H-indazol-1-amine maleate

A solution of N-(4-pyridinyl)-1H-indazol-1-amine (4 g) in 20 ml of dimethylformamide was slowly added to an ice-cooled suspension of sodium hydride prepared by washing 0.9 g of 60% NaH dispersion in oil with hexane and suspending the residue in 5 ml of dimethylformamide. After the anion formation a solution of 1-bromopropane (2.8 g) in 5 ml of dimethylformamide was added. After one hour the reaction mixture was stirred with ice-water and extracted with dichloromethane. The extract was washed with water and saturated sodium chloride solution, dried over anhydrous magnesium sulfate, filtered and concentrated to 5 g of oil. This oil was purified by flash chromatography to give 4 g of oil. This oil was converted to the maleate salt in ethanol-ether and thereafter recrystallized from methanol-ether to give 3.2 g of crystals, mp 119°–120°.

ANALYSIS: Calculated for $C_{15}H_{16}N_4 \cdot C_4H_4O_4$: 61.94%C, 5.47%H, 15.21%N. Found: 61.77%C, 5.41%H, 15.10%N.

EXAMPLE 6

N-(Propyl)-N-(4-pyridinyl)-2H-indazol-2-amine maleate

A solution of N-(4-pyridinyl)-2H-indazol-2-amine (5.2 g) in 30 ml of dimethylformamide was slowly added to an ice-cooled suspension of sodium hydride prepared by washing 1.2 g of 60% NaH dispersion in oil with hexane and suspending the residue in 10 ml of dimethylformamide. After the anion formation a solution of 1-bromopropane (3.7 g) in 5 ml of dimethylformamide was added. After one hour the reaction mixture was stirred with ice-water and extracted with dichloromethane. The extract was washed with water and saturated sodium chloride solution, dried over anhydrous magnesium sulfate, filtered and concentrated to 6 g of oil. This oil was purified by flash chromatography (silica, ethyl acetate) to give 5.2 g of yellow oil. This oil was converted to the maleate salt in ethanol-ether and recrystallized from methanol-ether to give 5.4 g of white crystals, mp 168°–169° d.

ANALYSIS: Calculated for $C_{15}H_{16}N_4 \cdot C_4H_4O_4$: 61.94%C, 5.47%H, 15.21%N. Found: 61.88%C, 5.71%H, 15.42%N.

We claim:

1. A compound of the formula

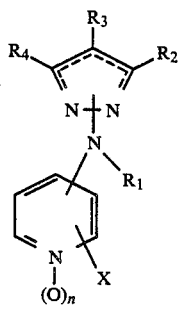

(I)

where n is 0 or 1; $R_1$ is independently hydrogen, loweralkyl, loweralkenyl, loweralkynyl, loweralkoxycarbonylloweralkyl, loweralkylaminocarbonylloweralkyl, aminocarbonylloweralkyl, arylloweralkyl, phenyl, nitrophenyl, cyanophenyl, trifluoromethylphenyl, aminophenyl, loweralkanoylaminophenyl, loweralkoxycarbonyl, arylloweralkoxycarbonyl, aryloxycarbonyl, loweralkylaminocarbonyl, arylloweralkylaminocarbonyl, arylaminocarbonyl, alkanoyl, arylloweralkanoyl, aroyl, alkenoyl, alkynoyl or —$R_5$—NR'R" where $R_5$ is loweralkylene, loweralkenylene or loweralkynylene and R' and R" are each independently loweralkyl or alternatively the group —NR'R" as a whole is 1-pyrrolidinyl, 1-piperidinyl, 4-morpholinyl, 4-loweralkyl-1-piperazinyl or 4-aryl-1-piperazinyl;

$R_2$ is hydrogen or loweralkyl;

$R_3$ and $R_4$ are each independently hydrogen or loweralkyl, or alternatively $R_3$ and $R_4$ taken together form —CH=CH—CH=CH— so that the moiety

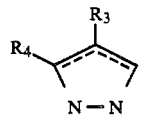

becomes an indazole ring; and

X is hydrogen, nitro, amino, halogen, loweralkanoylamino, arylloweralkanoylamino, aroylamino, alkylamino, arylloweralkylamino, loweralkyl, and cyano; the term aryl denotes a phenyl group having zero, one, two or three substituents each of which being independently lower alkyl, loweralkyl, halogen, $CF_3$, $NO_2$ or CN; the terms alkyl, alkenyl, alkynyl denote a chain of 1 to 20 carbon atoms or a pharmaceutically acceptable acid addition salt thereof.

2. The compound as defined in claim 1, where $R_1$ is hydrogen or loweralkyl.

3. The compound as defined in claim 1, where X is hydrogen or loweralkyl.

4. The compound as defined in claim 2, where X is hydrogen or loweralkyl.

5. The compound as defined in claim 1, where $R_2$ is hydrogen.

6. The compound as defined in claim 2, where $R_2$ is hydrogen.

7. The compound as defined in claim 3, where $R_2$ is hydrogen.

8. The compound as defined in claim 1, where $R_3$ and $R_4$ are both hydrogen.

9. The compound as defined in claim 2, where $R_3$ and $R_4$ are both hydrogen.

10. The compound as defined in claim 3, where $R_3$ and $R_4$ are both hydrogen.

11. The compound as defined in claim 5, where $R_3$ and $R_4$ are both hydrogen.

12. The compound as defined in claim 1, where $R_3$ and $R_4$ taken together form —CH=CH—CH=CH—.

13. The compound as defined in claim 2, where $R_3$ and $R_4$ taken together form —CH=CH—CH=CH—.

14. The compound as defined in claim 3, where $R_3$ and $R_4$ taken together form —CH=CH—CH=CH—.

15. The compound as defined in claim 5, where $R_3$ and $R_4$ taken together form —CH=CH—CH=CH—.

16. The compound as defined in claim 1, which is N-(1H-Pyrazol-1-yl)-4-pyridinamine.

17. The compound as defined in claim 1, which is N-(Propyl)-N-(1H-pyrazol-1-yl)-4-pyridinamine.

18. The compound as defined in claim 1, which is N-(4-Pyridinyl)-1H-indazol-1-amine.

19. The compound as defined in claim 1, which is N-(4-Pyridinyl)-2H-indazol-2-amine.

20. The compound as defined in claim 1, which is N-(Propyl)-N-(4-pyridinyl)-1H-indazol-1-amine.

21. The compound as defined in claim 1, which is N-(Propyl)-N-(4-pyridinyl)-2H-indazol-2-amine.

22. A pharmaceutical composition comprising an effective pain alleviating amount of a compound as defined in claim 1 and a suitable carrier therefor.

23. A pharmaceutical composition comprising an effective depression alleviating amount of a compound as defined in claim 1 and a suitable carrier therefor.

24. A method of treating a patient in need of relief from pain which comprises administering to the patient an effective pain alleviating amount of a compound as defined in claim 1.

25. A method of treating a patient in need of relief from depression which comprises administering to the patient an effective depression alleviating amount of a compound as defined in claim 1.

* * * * *